United States Patent
Thiberg

(10) Patent No.: US 6,238,424 B1
(45) Date of Patent: May 29, 2001

(54) DEVICE FOR EXTERNAL TREATMENT WITH PULSATING LIGHT OF HIGH DUTY CYCLE

(75) Inventor: Rolf Thiberg, Akersberga (SE)

(73) Assignee: Biolight Patent Holding AB, Danderyd (SE)

(*) Notice: Subject to any disclaimer, the term of this patent is extended or adjusted under 35 U.S.C. 154(b) by 0 days.

(21) Appl. No.: 09/194,972
(22) PCT Filed: Jun. 4, 1997
(86) PCT No.: PCT/SE97/00978
  § 371 Date: Dec. 7, 1998
  § 102(e) Date: Dec. 7, 1998
(87) PCT Pub. No.: WO97/46280
  PCT Pub. Date: Dec. 11, 1997

(30) Foreign Application Priority Data
  Jun. 7, 1996 (SE) .................................. 9602273

(51) Int. Cl.[7] .................................................... A61N 5/00
(52) U.S. Cl. .................................. 607/88; 606/9; 606/13; 607/89
(58) Field of Search ........................... 607/88–91, 93; 606/3, 9–13

(56) References Cited

U.S. PATENT DOCUMENTS

| | | | |
|---|---|---|---|
| 4,930,504 | * 6/1990 | Diamantopoulos et al. | 607/88 |
| 5,259,380 | 11/1993 | Mendes et al. | 607/115 |
| 5,358,503 | 10/1994 | Bertwell et al. | 606/27 |
| 5,500,009 | 3/1996 | Mendes et al. | 607/88 |
| 5,766,233 | * 6/1998 | Thiberg | 607/88 |
| 5,800,479 | * 9/1998 | Thiberg | 607/88 |

FOREIGN PATENT DOCUMENTS

| | | |
|---|---|---|
| 2548354 | 5/1977 | (DE) . |
| 2212010 | 7/1989 | (GB) . |
| WO9118646 | 12/1991 | (WO) . |
| WO9220403 | 11/1992 | (WO) . |
| WO9519809 | 7/1995 | (WO) . |
| WO9519810 | 7/1995 | (WO) . |

OTHER PUBLICATIONS

"Double Blind, Placebo–Controlled Investigation of the Effect of Combined Phototherapy/Low Intensity Laser Therapy Upon Experimental Ischaemic Pain in Humans", By Basim Mokhtar et al., *Lasers in Surgery and Medicine*, 17:74–81 (1995).

* cited by examiner

Primary Examiner—Michael Peffley
(74) Attorney, Agent, or Firm—Alfred J. Mangels

(57) ABSTRACT

Apparatus for external medical treatment with light. A light-emitting device is provided that is adapted to be held in close proximity to the body of an individual and that includes light-emitting diodes or corresponding elements that are adapted to emit monochromatic light of a first wavelength. The light emitting device is driven by a drive arrangement for causing the light-emitting device to emit the monochromatic light over a first predetermined time period in a first state, and thereafter emit selectively monochromatic light of a different wavelength than the first wavelength and over a second predetermined time period in a possible second state. The drive arrangement causes the light-emitting device to pulsate the emitted light in accordance with a predetermined pulse frequency or series of pulse frequencies over the respective time periods, and causes the light-emitting device to emit the pulsating light with a pulse length that lies within an interval of about 60% to about 90% of the time between respective start edges of two mutually sequential pulses.

9 Claims, 2 Drawing Sheets

DEVICE FOR EXTERNAL TREATMENT WITH PULSATING LIGHT OF HIGH DUTY CYCLE

The present invention relates to apparatus for external medical treatment with light, and more specifically light that will alleviate and/or cure different sicknesses, illnesses, diseases, etc., hereinafter referred to as health disorders.

It has been found that infrared light has a favourable effect in this regard.

Swedish Patent Specification No. 502 784 teaches apparatus for external medical treatment with light, comprising a light-emitting device which is intended to lie against or be held in the close proximity of the body of an individual, and drive means for driving the light-emitting device, wherein the light-emitting device includes light-emitting diodes or corresponding light-emitting elements and is adapted to emit infrared light. The invention according to this patent is mainly characterized in that the drive device is adapted to cause the light-emitting device to emit light over a predetermined period of time in a first stage, and thereafter to emit visible light over a second predetermined period of time in a second stage; and in that the drive device is adapted to cause the light-emitting device to pulsate the emitted infrared light and the visible light respectively in accordance with a predetermined series of pulse frequencies.

It has been found that such apparatus can be used very successfully in the treatment of other disorders and injuries, for instance injuries sustained in sporting activities, pulled or strained muscles, muscular pain, joint pains, headaches, different inflammatory conditions, different skin complaints, such as acne, back pains, etc., provided that the light is emitted in a certain way. Treatment with light has a favourable effect on the healing of injuries and will alleviate and/or cure various health disorders.

Thus, it is realized that treatment with light in which a certain light is emitted in a certain series of frequencies will have a significantly greater effect with respect to shortening the time taken to cure or alleviate a health disorder.

It has also been found that treatment with solely one or more monochromatic lights other than infrared light, such as visible light of different colours, emitted in accordance with a certain pulse frequency give a very good treatment result.

The present invention is based on the insight that the pulse length of emitted pulsating light of a given pulse frequency has a great effect on the result of the treatment.

The present invention thus relates to apparatus for external medical treatment with light, wherein the apparatus includes a light-emitting device which is intended to lie against or to be held in the close proximity of the body of an individual, and a drive device for driving the light-emitting device, wherein the light-emitting device includes light-emitting diodes or corresponding elements and is adapted to emit monochromatic light of a first wavelength, wherein the drive device is adapted to cause the light-emitting device to emit said monochromatic light over a predetermined first time period in a first state, and thereafter to emit selectively monochromatic light of a different wavelength to the first wavelength over a second predetermined time period in a possible second stage, and wherein the drive device is adapted to cause the light-emitting device to pulsate said emitted light in accordance with a predetermined pulse frequency or series of pulse frequencies over said time periods, and wherein the apparatus is characterized in that the drive device is adapted to cause the light-emitting devices to emit said pulsating light with a pulse length that lies within an interval of about 60% to 90% of the time between respective start edges of two mutually sequential pulses.

The invention will now be described in more detail with reference to exemplifying embodiments thereof and also with reference to the accompanying drawings, wherein FIG. 1 illustrates the inventive apparatus schematically and in block form;

Figure 1:
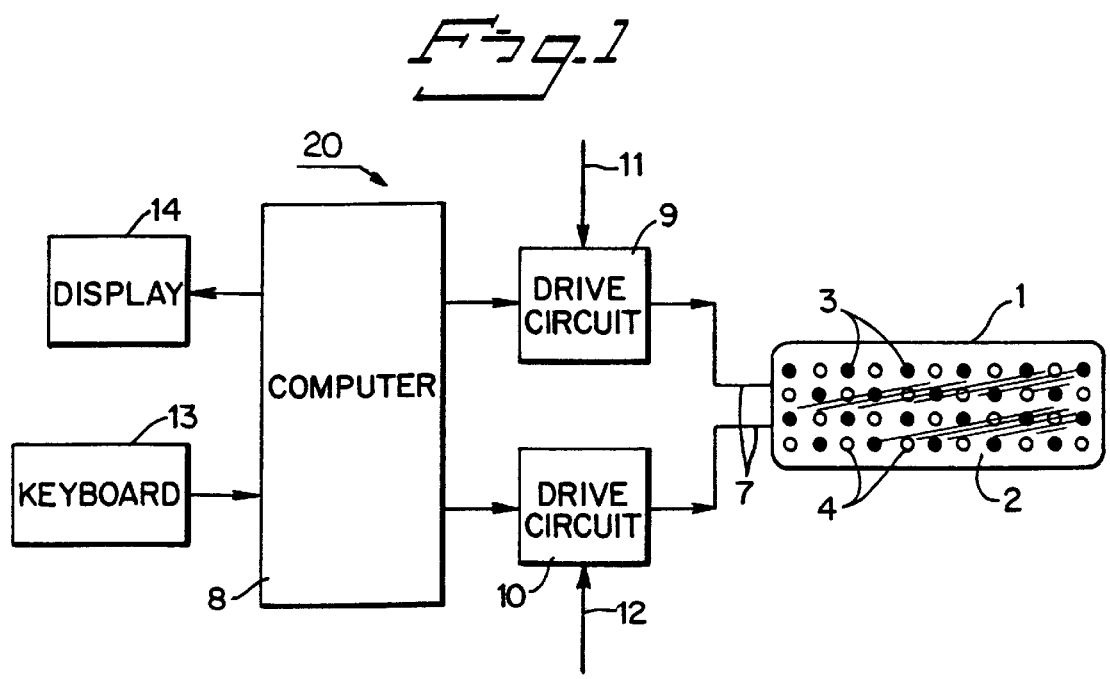
Figure 2:
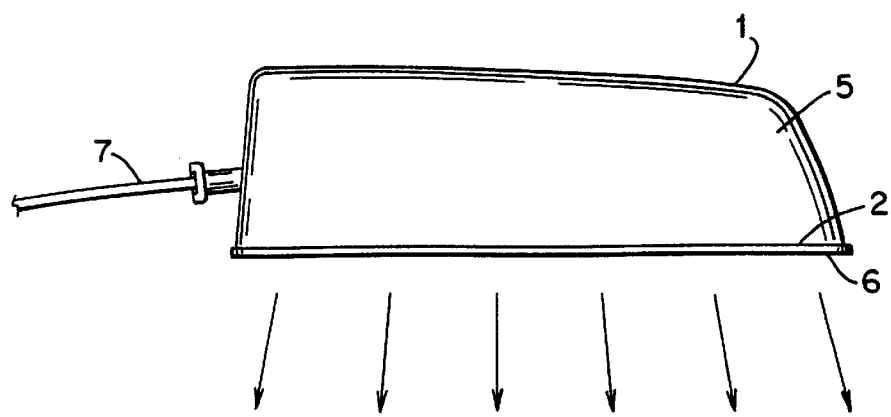
FIG. 2 is a side view of a light-emitting device.

FIGS. 1 and 2 illustrate apparatus for external medical treatment with the aid of light. The apparatus includes a light-emitting device 1, which is intended to lie against or to be held in the close proximity of the body of an individual. FIG. 2 shows the light-emitting device from one side, while FIG. 1 shows the element from beneath. The light-emitting device includes a housing 5 which is provided with a transparent plate 6. Located beneath the plate 6 is a surface 2 on which a plurality of light-emitting diodes 3, 4 or corresponding light-emitting elements are mounted. The light-emitting diodes send light through the plate 6 when the diodes are energized, i.e. supplied with current through a cable 7. In use, the housing 5 is held so that the plate 6 will lie against the relevant part of the body. The apparatus also includes drive means 8, 9, 10 for driving the light-emitting device 1. The light-emitting device 1 may include light-emitting diodes 3 or corresponding means for emitting infrared light. These diodes or the like are marked with solid circles in FIG. 1.

The drive means 8, 9, 10 are adapted to cause the light-emitting device 1 to emit monochromatic light of a given wavelength over a predetermined time period. The drive means may also be adapted to emit monochromatic light of a wavelength different to the first-mentioned wavelength over a second predetermined time period, in an optional second stage of the treatment. Visible light is emitted with the aid of light-emitting diodes 4 or corresponding elements. These diodes are marked with hollow circles in FIG. 1.

The drive means 8, 9, 10 are also adapted to cause the light-emitting device 1 to emit pulsating light in accordance with a predetermined pulse frequency or a series of pulse frequencies over predetermined time periods. The drive means include a computer 8 which functions to control drive circuits 9, 10, to which voltage is applied for driving the light-emitting diodes via conductors 11, 12.

The computer and drive circuits are of an appropriate known kind. Connected to the drive means is a keyboard 13 by means of which the operator can enter drive means control data for actuating the light-emitting device in a desired manner. The apparatus will also conveniently include a display 14, on which the settings made through the keyboard are displayed.

Infrared light-emitting diodes 3 are preferably semiconductor diodes of the GaAs kind (Gallium arsenide). The light-emitting diodes 4 that emit visible light are also preferably of the GaAs type.

For instance, the number of light-emitting diodes included in the light-emitting device may be such that the infrared light-emitting diodes will together generate a light power of 1800 milliwatts, and the diodes that emit visible light may each have a power of 3000 millicandela.

According to one embodiment of the invention, the light-emitting device 1 includes red light emitting diodes 4 that emit visible light at the wavelength of 660 nanometers and/or infrared light emitting diodes that emit light at the wavelength of 950 nanometers.

In another embodiment of the invention, the light-emitting device 1 includes light-emitting diodes 4 that emit a substantially monochromatic visible light in one of the colours violet, blue, yellow, orange, red or green.

The visible light used will depend on the disorder or type of injury to be treated.

The subject matter described above with reference to the accompanying drawings is essentially also found described in the aforementioned patent specification.

According to the invention, the drive device is adapted to cause the light-emitting device or elements to emit said pulsating monochromatic light at a pulse length that lies within an interval of about 60% to 90% of the time between respective start edges 18, 19 of two mutually sequential pulses 15.

Figure 4:
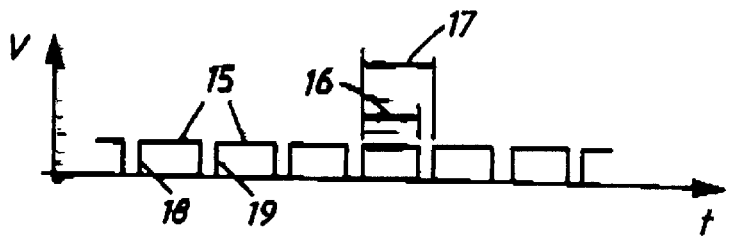
FIG. 4 illustrates pulsated light.

FIG. 4 is a schematic illustration of emitted light pulses, where amplitude V is shown on the Y-axis and time t on the X-axis. The duration of a pulse 15 is referenced 16 and the total pulse time plus a subsequent pause is referenced 17.

Figure 3:
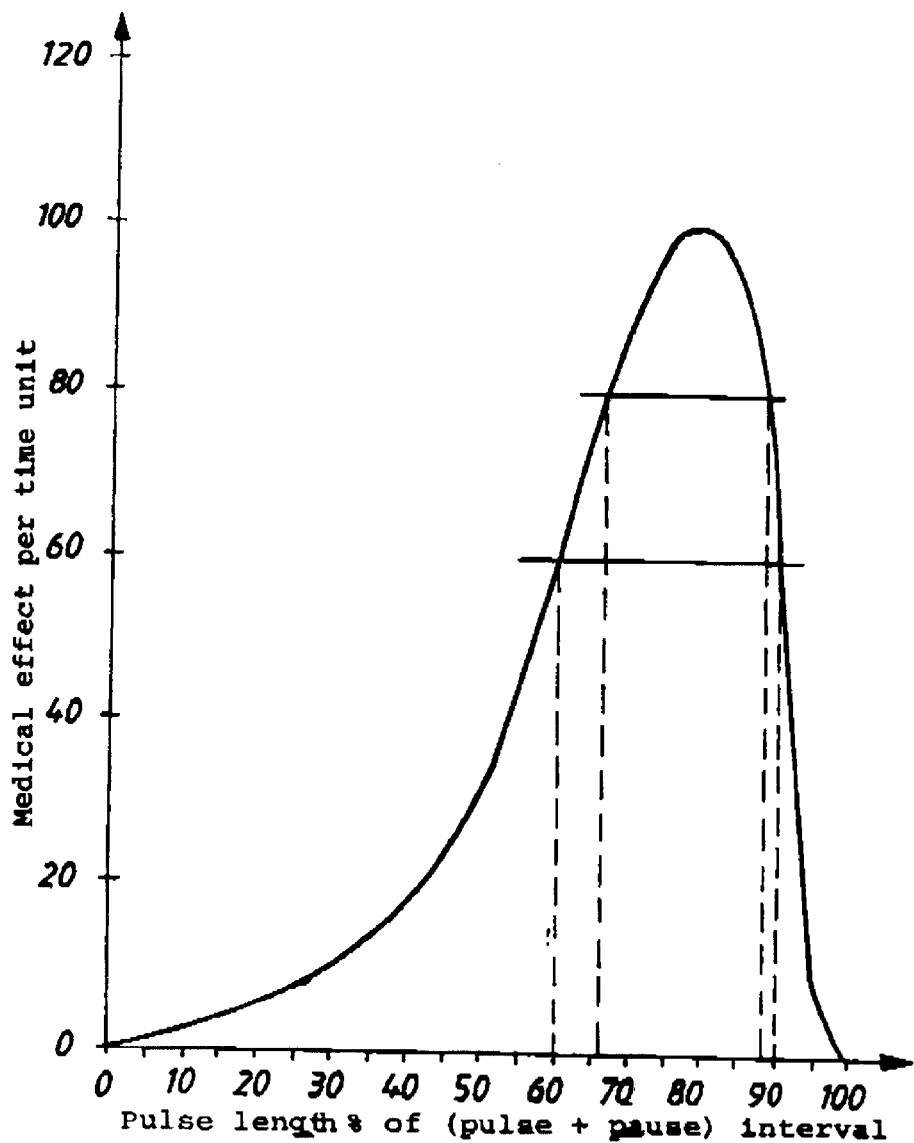
FIG. 3 is a diagram.

The medical effect per unit of time is shown on the Y-axis of the diagramme in FIG. 3. This is a subjective measurement of the medical effect achieved, but is a result of tests of long duration and can therefore be considered highly reliable. The maximum value of the Y-axis is 100%. The X-axis shows the pulse length 16 as a percentage of the total time 17 of a pulse plus a subsequent pause, i.e. there is no pause between the pulses.

As FIG. 3 surprisingly shows, the curve has a maximum at a value of about 79% on the X-axis, whereafter the curve falls steeply to zero with respect to medical effect.

The treatment interval is therewith relatively narrow, and lies between 60% and 90% on the X-axis. A medical effect of at lowest 60% is obtained within this interval.

However, the interval is narrower in accordance with one preferred embodiment. According to this preferred embodiment, the pulse length lies within an interval of about 67% to 88% of the time between respective start edges of two mutually sequential pulses, i.e. from 67% to 88% on the X-axis. The medical effect is at lowest 80% within this interval.

It will be evident that realization of the circumstances reflected in FIG. 3 are of the greatest significance in the external medical treatment of disorders and injuries with light. The present invention thus provides considerable advances in this field. It should be mentioned that application of the present invention is not restricted to the treatment of patients in accordance with the prior patent publication mentioned in the introduction but can also be applied in the acupuncture treatment of patients with light as described in Swedish Patent Specification No. 9602272-8.

The present invention is not therefore restricted to the aforedescribed and illustrated exemplifying embodiments thereof, since modifications and variations can be made within the scope of the following claims.

What is claimed is:

1. Apparatus for external medical treatment with light, said apparatus comprising: a light-emitting device which is adapted to be held in close proximity to the body of an individual to be treated, wherein the light-emitting device includes light-emitting elements for emitting monochromatic light of substantially only one wavelength during a predetermined time interval, and drive means for driving the light-emitting device, wherein the drive means includes means for controlling the light-emitting device to emit said monochromatic light of substantially only one wavelength over a predetermined treatment time period, and wherein the drive means includes means for controlling the light-emitting device to pulsate said emitted monochromatic light of substantially only one wavelength in accordance with a predetermined pulse frequency over said time period, and wherein the drive means includes means for controlling said light-emitting devices to emit said pulsating monochromatic light of substantially only one wavelength with a pulse length that lies within an interval of about 67% to about 88% of the time between respective start edges of two mutually sequential pulses.

2. Apparatus according to claim 1, wherein the light-emitting device is adapted to lie against the body of the individual to be treated.

3. Apparatus according to claim 1, wherein the light-emitting device includes light-emitting diodes.

4. Apparatus according to claim 1, wherein the drive means includes means for controlling the light-emitting device to emit monochromatic light of a second, different wavelength for a second time period in a second treatment stage.

5. Apparatus according to claim 1, wherein the drive means includes means for controlling the light-emitting device to emit monochromatic light in accordance with a predetermined series of pulse frequencies.

6. Apparatus according to claim 1, wherein the light-emitting device emits visible light at a wavelength of about 660 nanometers.

7. Apparatus according to claim 1, wherein the light-emitting device emits infrared light at a wavelength of about 950 nanometers.

8. Apparatus according to claim 4, wherein the light-emitting device emits visible light at a wavelength of about 660 nanometers during a first treatment state and emits infrared light at a wavelength of about 950 nanometers during the second treatment stage.

9. Apparatus according to claim 4, wherein the light-emitting device emits infrared light at a wavelength of about 950 nanometers during a first treatment stage and emits visible light at a wavelength of about 660 nanometers during the second treatment stage.

* * * * *